(12) United States Patent
Morris et al.

(10) Patent No.: US 8,118,832 B1
(45) Date of Patent: Feb. 21, 2012

(54) METHOD AND APPARATUS FOR SEALING ACCESS

(75) Inventors: Edward J. Morris, Bloomington, IN (US); Andrew J. DeNardo, Carmel, IN (US)

(73) Assignee: Morris Innovative, Inc., Bloomington, IN (US)

( * ) Notice: Subject to any disclaimer, the term of this patent is extended or adjusted under 35 U.S.C. 154(b) by 241 days.

(21) Appl. No.: 12/484,538

(22) Filed: Jun. 15, 2009

Related U.S. Application Data

(60) Provisional application No. 61/061,823, filed on Jun. 16, 2008.

(51) Int. Cl.
*A61B 17/03* (2006.01)

(52) U.S. Cl. ...................................................... 606/213

(58) Field of Classification Search .................. 606/153, 606/213, 214–217, 144, 154, 108; 623/1.23, 623/1.38, 23.72; 604/15–18, 59–64, 93.01, 604/174, 175, 181
See application file for complete search history.

(56) References Cited

U.S. PATENT DOCUMENTS

| | | |
|---|---|---|
| 3,562,820 A | 2/1971 | Braun |
| 4,520,821 A | 6/1985 | Schmidt et al. |
| 4,837,379 A | 6/1989 | Weinberg |
| 4,838,280 A | 6/1989 | Haaga |
| 4,852,568 A | 8/1989 | Kensey |
| 4,890,612 A | 1/1990 | Kensey |
| 4,902,508 A | 2/1990 | Badylak et al. |
| 5,021,059 A | 6/1991 | Kensey et al. |
| 5,061,274 A | 10/1991 | Kensey |
| 5,106,949 A | 4/1992 | Kemp et al. |
| 5,108,421 A | 4/1992 | Fowler |
| 5,151,105 A | 9/1992 | Kwan-Gett |
| 5,163,955 A | 11/1992 | Love et al. |
| 5,192,302 A | 3/1993 | Kensey et al. |
| 5,222,974 A | 6/1993 | Kensey et al. |
| 5,254,105 A | 10/1993 | Haaga |
| 5,256,418 A | 10/1993 | Kemp et al. |
| 5,275,826 A | 1/1994 | Badylak et al. |
| 5,281,422 A | 1/1994 | Badylak et al. |
| 5,282,827 A | 2/1994 | Kensey et al. |
| 5,292,332 A | 3/1994 | Lee |
| 5,306,254 A | 4/1994 | Nash et al. |
| 5,310,407 A | 5/1994 | Casale |
| 5,312,435 A | 5/1994 | Nash et al. |
| 5,342,393 A | 8/1994 | Stack |
| 5,370,660 A | 12/1994 | Weinstein et al. |

(Continued)

FOREIGN PATENT DOCUMENTS

EP 0 604 761 B1 7/1994

(Continued)

OTHER PUBLICATIONS

International Search Report and Written Opinion for PCT Application No. PCT/US2009/047348, issued Jun. 29, 2009, 8 pgs.

*Primary Examiner* — Ryan Severson
*Assistant Examiner* — Rachel S Papeika
(74) *Attorney, Agent, or Firm* — Faegre Baker Daniels LLP

(57) ABSTRACT

An apparatus and a method for sealing a puncture in a tubular tissue structure or the wall of a body cavity are provided. The apparatus and method include a bioabsorbable member that is partially external to and partially internal to an introducer sheath before and during placement thereof.

37 Claims, 5 Drawing Sheets

U.S. PATENT DOCUMENTS

| | | |
|---|---|---|
| 5,376,376 A | 12/1994 | Li |
| 5,378,469 A | 1/1995 | Kemp et al. |
| RE34,866 E | 2/1995 | Kensey et al. |
| 5,391,183 A | 2/1995 | Janzen et al. |
| 5,403,278 A | 4/1995 | Ernst et al. |
| 5,411,520 A | 5/1995 | Nash et al. |
| 5,413,571 A | 5/1995 | Katsaros et al. |
| 5,437,631 A | 8/1995 | Janzen |
| 5,441,517 A | 8/1995 | Kensey et al. |
| 5,531,759 A | 7/1996 | Kensey et al. |
| 5,540,715 A | 7/1996 | Katsaros et al. |
| 5,545,178 A | 8/1996 | Kensey et al. |
| 5,545,180 A | 8/1996 | Le et al. |
| 5,549,633 A | 8/1996 | Evans et al. |
| 5,554,389 A | 9/1996 | Badylak et al. |
| 5,591,204 A | 1/1997 | Janzen et al. |
| 5,630,833 A | 5/1997 | Katsaros et al. |
| 5,649,959 A | 7/1997 | Hannam et al. |
| 5,662,681 A | 9/1997 | Nash et al. |
| 5,676,689 A | 10/1997 | Kensey et al. |
| 5,676,698 A | 10/1997 | Janzen et al. |
| 5,681,334 A | 10/1997 | Evans et al. |
| 5,690,674 A | 11/1997 | Diaz |
| 5,700,277 A | 12/1997 | Nash et al. |
| 5,707,393 A | 1/1998 | Kensey et al. |
| 5,711,969 A | 1/1998 | Patel et al. |
| 5,725,498 A | 3/1998 | Janzen et al. |
| 5,728,114 A | 3/1998 | Evans et al. |
| 5,733,337 A | 3/1998 | Carr et al. |
| 5,741,223 A | 4/1998 | Janzen et al. |
| 5,830,130 A | 11/1998 | Janzen et al. |
| 5,861,004 A | 1/1999 | Kensey et al. |
| 5,873,854 A | 2/1999 | Wolvek |
| 5,906,631 A | 5/1999 | Imran |
| 5,916,236 A | 6/1999 | Van De Moer et al. |
| 5,922,022 A | 7/1999 | Nash et al. |
| 5,922,024 A | 7/1999 | Janzen et al. |
| 5,928,266 A | 7/1999 | Kontos |
| 5,935,147 A | 8/1999 | Kensey et al. |
| 5,948,425 A | 9/1999 | Janzen et al. |
| 5,980,548 A | 11/1999 | Evans et al. |
| 5,993,452 A | 11/1999 | Vandewalle |
| 5,997,896 A | 12/1999 | Carr et al. |
| 6,007,563 A | 12/1999 | Nash et al. |
| 6,017,352 A | 1/2000 | Nash et al. |
| 6,030,395 A | 2/2000 | Nash et al. |
| 6,036,705 A | 3/2000 | Nash et al. |
| 6,045,569 A | 4/2000 | Kensey et al. |
| 6,056,762 A | 5/2000 | Nash et al. |
| 6,063,114 A | 5/2000 | Nash et al. |
| 6,090,130 A | 7/2000 | Nash et al. |
| 6,099,567 A | 8/2000 | Badylak et al. |
| 6,110,459 A | 8/2000 | Mickle et al. |
| 6,146,372 A | 11/2000 | Leschinsky et al. |
| 6,179,863 B1 | 1/2001 | Kensey et al. |
| 6,183,496 B1 | 2/2001 | Urbanski |
| 6,190,400 B1 | 2/2001 | Van De Moer et al. |
| 6,203,556 B1 | 3/2001 | Evans et al. |
| 6,261,309 B1 | 7/2001 | Urbanski |
| 6,264,701 B1 | 7/2001 | Brekke |
| 6,325,789 B1 | 12/2001 | Janzen et al. |
| 6,334,872 B1 | 1/2002 | Termin et al. |
| 6,346,092 B1 | 2/2002 | Leschinsky |
| 6,350,280 B1 | 2/2002 | Nash et al. |
| 6,358,284 B1 | 3/2002 | Fearnot et al. |
| 6,368,341 B1 | 4/2002 | Abrahamson |
| 6,391,036 B1 | 5/2002 | Berg et al. |
| 6,402,767 B1 | 6/2002 | Nash et al. |
| 6,475,232 B1 | 11/2002 | Babbs et al. |
| 6,494,848 B1 | 12/2002 | Sommercorn et al. |
| 6,497,686 B1 | 12/2002 | Adams et al. |
| 6,514,271 B2 | 2/2003 | Evans et al. |
| 6,537,254 B1 | 3/2003 | Schock et al. |
| 6,551,283 B1 | 4/2003 | Guo et al. |
| 6,569,147 B1 | 5/2003 | Evans et al. |
| 6,572,650 B1 | 6/2003 | Abraham et al. |
| 6,623,460 B1 | 9/2003 | Heck |
| 6,623,509 B2 | 9/2003 | Ginn |
| 6,632,200 B2 | 10/2003 | Guo et al. |
| 6,660,015 B1 | 12/2003 | Berg et al. |
| 6,673,084 B1 | 1/2004 | Peterson et al. |
| 6,709,427 B1 | 3/2004 | Nash et al. |
| 6,749,617 B1 | 6/2004 | Palasis et al. |
| 6,758,854 B1 | 7/2004 | Butler et al. |
| 6,759,245 B1 | 7/2004 | Toner et al. |
| 6,764,500 B1 | 7/2004 | Van De Moer et al. |
| 6,790,220 B2 | 9/2004 | Morris et al. |
| 7,361,183 B2 | 4/2008 | Ginn |
| 2001/0003158 A1 | 6/2001 | Kensey et al. |
| 2001/0041928 A1 | 11/2001 | Pavcnik et al. |
| 2001/0053932 A1 | 12/2001 | Phelps et al. |
| 2002/0072768 A1 | 6/2002 | Ginn |
| 2002/0077656 A1 | 6/2002 | Ginn et al. |
| 2002/0183786 A1 | 12/2002 | Girton |
| 2005/0065549 A1 | 3/2005 | Cates et al. |
| 2006/0009802 A1 | 1/2006 | Modesitt |
| 2007/0038244 A1* | 2/2007 | Morris et al. .................. 606/213 |
| 2007/0038245 A1 | 2/2007 | Morris et al. |

FOREIGN PATENT DOCUMENTS

| | | |
|---|---|---|
| EP | 0 818 178 B1 | 1/1998 |
| WO | WO 90/00395 | 1/1990 |
| WO | WO 93/08743 | 5/1993 |
| WO | WO 93/25255 | 12/1993 |
| WO | WO 96/31157 | 10/1996 |
| WO | WO 98/22158 | 5/1998 |
| WO | WO 01/45765 | 6/2001 |
| WO | WO 02/100245 | 12/2002 |

* cited by examiner

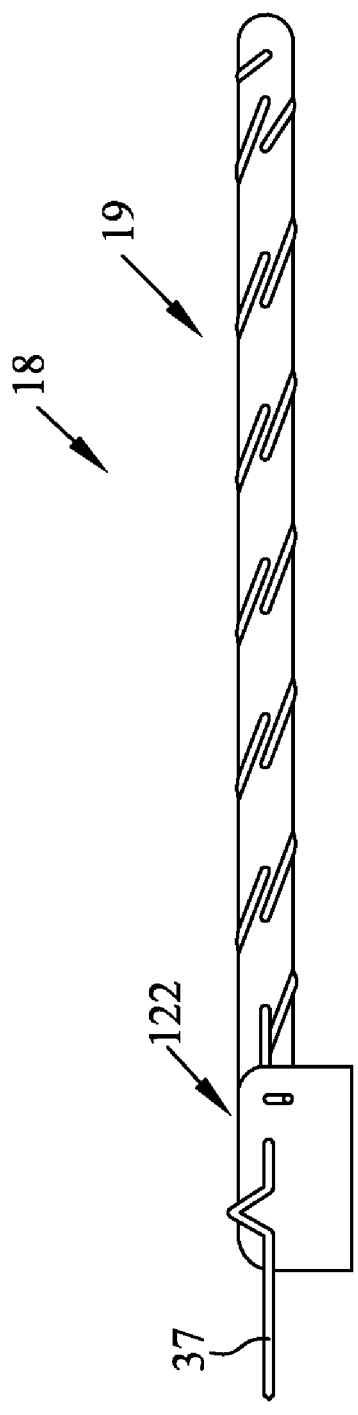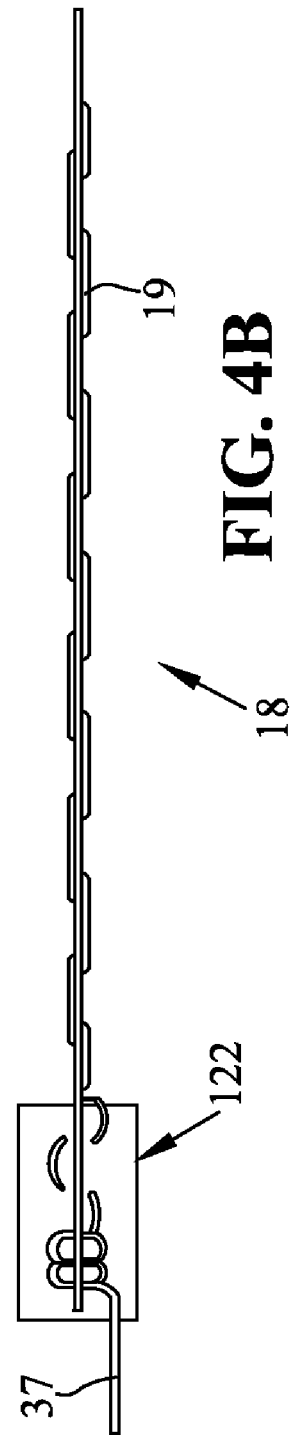
FIG. 4A
FIG. 4B

METHOD AND APPARATUS FOR SEALING ACCESS

CLAIM FOR PRIORITY

The present application claims priority to U.S. Provisional Application 61/061,823 filed Jun. 16, 2008, the disclosure of which is incorporated herein by reference.

FIELD OF THE DISCLOSURE

The present disclosure relates to an apparatus and a method for sealing a puncture in a tubular tissue structure or the wall of a body cavity. More particularly, the present disclosure is directed to sealing a puncture site with submucosal tissue or another extracellular matrix-derived tissue capable of remodeling endogenous connective tissue or with a synthetic bioabsorbable material.

BACKGROUND AND SUMMARY

The control of bleeding during and after surgery is important to the success of the procedure. The control of blood loss is of particular concern if the surgical procedure is performed directly upon or involves the patient's arteries and veins. Well over one million surgical procedures are performed annually which involve the insertion and removal of catheters into and from arteries and veins. Accordingly, these types of vasculature procedures represent a significant amount of surgery in which the control of bleeding is of particular concern.

Typically, the insertion of a catheter creates a puncture through the vessel wall and upon removal the catheter leaves a puncture opening through which blood may escape and leak into the surrounding tissues. Therefore, unless the puncture site is closed clinical complications may result leading to increased hospital stays with the associated costs. To address this concern, medical personnel are required to provide constant and continuing care to a patient who has undergone a procedure involving an arterial or venous puncture to insure that post-operative bleeding is controlled.

Surgical bleeding concerns can be exacerbated by the administration of a blood thinning agent, such as heparin, to the patient prior to a catheterization procedure. Since the control of bleeding in anti-coagulated patients is much more difficult to control, stemming blood flow in these patients can be troublesome. A common method of healing the puncture to the vessel is to maintain external pressure over the vessel until the puncture seals by natural clot formation processes. This method of puncture closure typically takes about thirty to ninety minutes, with the length of time usually being greater if the patient is hypertensive or anti-coagulated.

Furthermore, it should be appreciated that utilizing pressure, such as human hand pressure, to control bleeding suffers from several drawbacks regardless of whether the patient is hypertensive or anti-coagulated. In particular, when human hand pressure is utilized, it can be uncomfortable for the patient, can result in excessive restriction or interruption of blood flow, and can use costly professional time on the part of the hospital staff. Other pressure techniques, such as pressure bandages, sandbags, or clamps require the patient to remain motionless for an extended period of time and the patient must be closely monitored to ensure the effectiveness of these techniques.

Other devices have been disclosed which plug or otherwise provide an obstruction in the area of the puncture (see, for example, U.S. Pat. Nos. 4,852,568 and 4,890,612) wherein a collagen plug is disposed in the blood vessel opening. When the plug is exposed to body fluids, it swells to block the wound in the vessel wall. A potential problem with plugs introduced into the vessel is that particles may break off and float downstream to a point where they may lodge in a smaller vessel, causing an infarct to occur. Another potential problem with collagen plugs is that there is the potential for the inadvertent insertion of the collagen plug into the lumen of the blood vessel which is hazardous to the patient. Collagen plugs also can act as a site for platelet aggregation, and, therefore, can cause intraluminal deposition of occlusive material creating the possibility of a thrombosis at the puncture sight. Other plug-like devices are disclosed, for example, in U.S. Pat. Nos. 5,342,393, 5,370,660 and 5,411,520.

Accordingly, there is a need for surgical techniques suitable for sealing punctures in a tubular tissue structure or in the punctured wall of a body cavity, such as a heart chamber, or a body cavity of another organ. Such techniques require rapid, safe, and effective sealing of the puncture. It would also be useful to close the puncture without disposing any occlusive material into the vessel or body cavity, and without introducing infectious organisms into the patient's circulatory system.

The present disclosure is directed to an apparatus and method for sealing punctured tubular tissue structures, including arteries and veins, such as punctures which occur during diagnostic and interventional vascular and peripheral catheterizations, or for sealing a puncture in the wall of a body cavity. More specifically, the apparatus and method of the present disclosure employ submucosal tissue or another extracellular matrix-derived tissue or a synthetic bioabsorbable material to seal punctures in tubular tissue structures, such as blood vessels, or in the wall of a body cavity. The submucosal tissue or other extracellular matrix-derived tissue is capable of inducing tissue remodeling at the site of implantation by supporting the growth of connective tissue in vivo, and has the added feature of being tear-resistant so that occlusive material is not introduced into the patient's circulatory system. Also, submucosal tissue or another extracellular matrix-derived tissue has the feature of being resistant to infection, thereby reducing the chances that the procedure will result in systemic infection of the patient.

In one embodiment, a device for sealing a puncture site in the wall of a body is provided. The device comprising an elongated element having a tissue wall contact exterior portion and having a length adapted to be inserted into the puncture site so that the length forms intravascular, intermediate and extracorporeal portions, and a bioabsorbable member releasably attached to the tissue wall contact exterior portion of the elongated element.

In another embodiment a device for sealing a puncture site in the wall of a blood vessel is provided. The device comprising an elongated element having a tissue wall contact exterior portion and a bioabsorbable member releasably attached to the tissue wall contact exterior portion of the elongated element.

In an alternate embodiment a method of sealing a puncture site in tissue is disclosed. The method comprises the steps of providing an elongated element having a bioabsorbable member disposed on the exterior thereof, the elongated element being configured to be introduced into a body with the bioabsorbable member disposed thereon; and providing a deposit member that allows the bioabsorbable member to be left within a body when the elongated element is removed from the body.

In another embodiment a method of sealing a puncture site in the wall of a body cavity is provided. The method comprises the step of providing an access device having an elongated element having a lumen therein and a tissue wall contact exterior portion and having a bioabsorbable member releasably disposed on the tissue wall contact exterior portion of the elongated element; placing the access device in contact with tissue; locating an instrument within the lumen of the elongated element; releasing the bioabsorbable member from the elongated element; and removing the elongated element from contact with tissue while allowing the bioabsorbable member to remain in contact with the tissue.

BRIEF DESCRIPTION OF THE DRAWINGS

FIGS. 2 & 2A illustrates the introducer element of FIG. 1 with a graft sheet deployed therefrom;

FIGS. 4A & 4B show the graft sheet and tether attached thereto; and

DETAILED DESCRIPTION

The disclosures of U.S. application Ser. Nos. 11/180,379, 10/863,703, 10/166,399, 11/879,426, 11/546,079, and 60/297,060 are incorporated herein by reference. The present disclosure is related to an apparatus and a method for sealing a puncture in a tubular tissue structure, such as a blood vessel, or in the wall of a body cavity, with submucosal tissue, another extracellular matrix-derived tissue, or a synthetic bioabsorbable material capable of supporting the growth of endogenous connective tissue in vivo resulting in remodeling of endogenous connective tissue at the puncture site and in formation of a static seal. The apparatus and method of the present disclosure can be used to seal a puncture in a tubular tissue structure, such as a blood vessel, or in the wall of a body cavity, that has been created intentionally or unintentionally during a surgical procedure or nonsurgically (e.g., during an accident). Punctures made intentionally include vascular punctures made in various types of vascular, endoscopic, or orthopaedic surgical procedures, or punctures made in any other type of surgical procedure, in coronary and in peripheral arteries and veins or in the wall of a body cavity. Such procedures include angiographic examination, angioplasty, laser angioplasty, valvuloplasty, atherectomy, stent deployment, rotablator treatment, aortic prosthesis implantation, intraortic balloon pump treatment, pacemaker implantation, any intracardiac procedure, electrophysiological procedures, interventional radiology, and various other diagnostic, prophylactic, and therapeutic procedures such as dialysis and procedures relating to percutaneous extracorporeal circulation.

Figure 1:
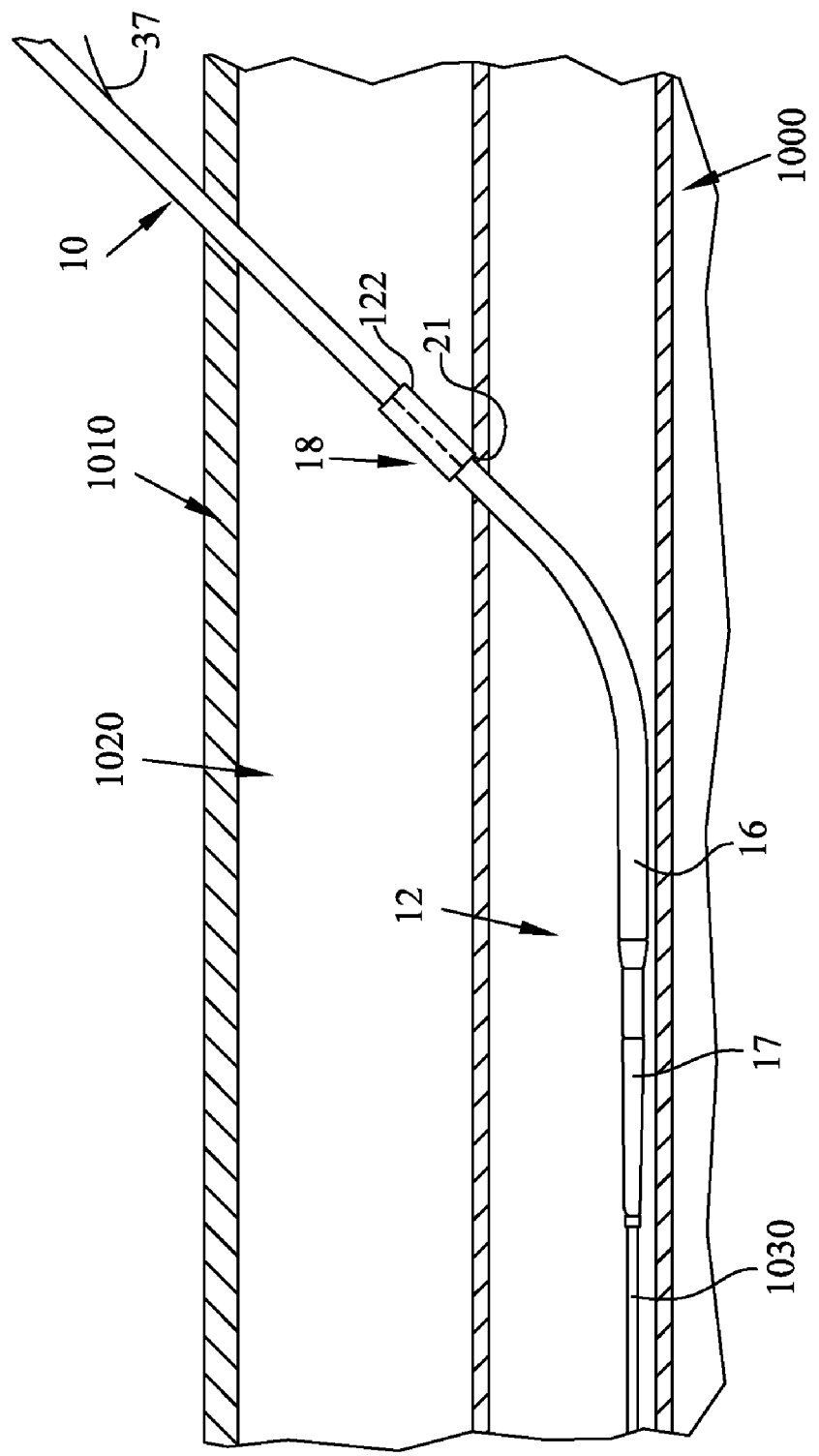
FIG. 1 illustrates an introducer element for use in sealing access to a tubular tissue structure or a body cavity partially disposed in a tubular tissue structure.

Referring now to the drawings, FIG. 1 illustrates an introducer 10 adapted for catheterization, exemplary of the type of introducer element that may be used in accordance with the present disclosure. Although an introducer 10 adapted for use in catheterization procedures is illustrated in FIG. 1, it is understood that the present disclosure is applicable to any type of introducer element used to provide access to the lumen of a tubular tissue structure, such as a blood vessel, or to a body cavity. For example, the present disclosure is applicable to an introducer element such as a needle, a cannula, a guide wire, an introducer element adapted for dialysis, a trocar, or any other introducer element used to access the lumen of a tubular tissue structure or a body cavity.

An introducer 10 as depicted in FIG. 1 can be used when performing catheterization procedures in coronary and peripheral arteries and veins 1000. Typically, a catheter is introduced into the vascular system by first penetrating the skin 1010, underlying muscle tissue 1020, and the blood vessel 1000 with a needle, and guide wire 1030 is inserted through the lumen of the needle and enters the blood vessel. Subsequently, the needle is stripped off the guide wire and introducer 10 is fed over guide wire 1030 and pushed through skin 1010 and through the vessel wall to enter vessel 1000. Guide wire 1030 can then be removed and a catheter is fed through the lumen of the introducer 10 and advanced through the vascular system until the working end of the catheter is positioned at a predetermined location. Alternatively, guide wire 1030 may be left in place throughout the procedure and the introducer 10 removed before guide wire 1030 is removed. At the end of the catheterization procedure, the catheter is withdrawn. Introducer 10 is also removed and the opening through which, for example, introducer 10 is inserted must be sealed as quickly as possible once the procedure is completed. Although a typical catheterization procedure utilizing introducer 10 is described, the described procedure is non-limiting. Furthermore any embodiment of introducer 10 described below is applicable to any other introducer element for use in accessing the lumen of a tubular tissue structure or a body cavity.

The present disclosure may be employed, for example, to rapidly seal a puncture site in a blood vessel upon completion of a catheterization procedure. Introducer 10 illustrated in FIG. 1 is an exemplary embodiment and has a user distal end 12 for insertion into blood vessel 1000 and a user proximal end 14. A standard introducer comprises dilator 17 and sheath 16 which extends axially over dilator 17, sheath cap 20 disposed axially over a portion of sheath 16 and valve cap 22 connected to sheath cap 20 and to side port tube 24. Dilator 17 includes a section of decreased diameter (not shown) that provides clearance within sheath 16 for flexible portion 19 of sheet 18 when flexible portion 19 is disposed within sheath 16 as discussed below. A standard introducer may also comprise three-way valve 26 connected to an end of the side port tube 24, and syringe connector 28, adapted for the attachment of a syringe to introducer 10 and connected to valve cap 22. Although not part of a standard introducer, introducer 10 depicted in FIG. 1 further comprises sheet 18 of submucosal tissue or another extracellular matrix-derived tissue or a synthetic bioabsorbable material extending axially over a portion of sheath 16.

In the embodiment of the disclosure depicted in FIG. 1, sheet 18 of submucosal tissue or another extracellular matrix-derived tissue or a synthetic bioabsorbable material includes cuff section 122 that extends axially over a portion of sheath 16. Sheet 18 further includes flexible section 19 at a user distal end 30 that is disposed within sheath 16 prior to deployment. To this end, sheath 16 includes an access hole 21 that receives flexible section 19 therein while allowing cuff section 122 to remain outside and around sheath 16. Distal end 30 of sheath 16 is inserted into tubular tissue structure 1000, such as a blood vessel, and user proximal end 32 remains outside of the punctured vessel wall. Proximal end 32, cuff 122, of the sheet 18 extends axially over a portion of the introducer 10 as depicted in FIG. 1.

Figure 5A:
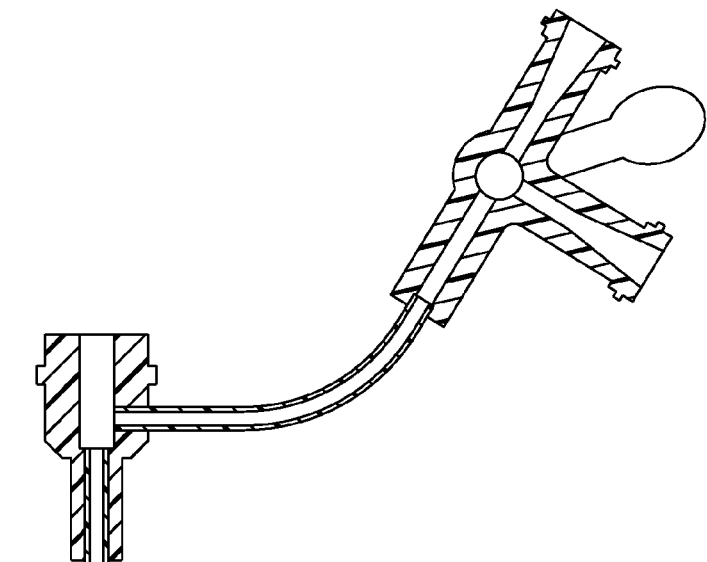
FIGS. 5A & 5B show the introducer element and graft sheet outside of the anatomy and pre-deployment.
Figure 5B:
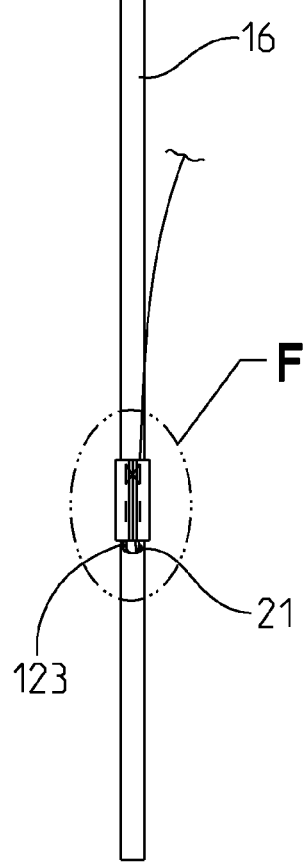
Figure 5B:
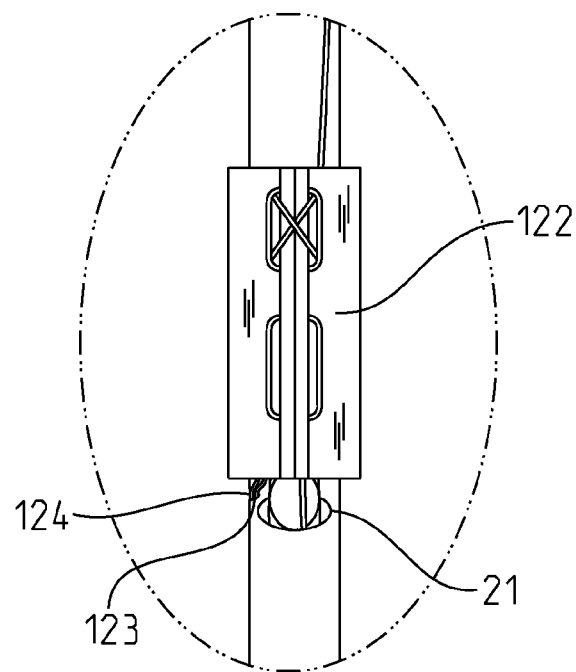

Cuff section 122 of sheet 18 may be held in place on sheath 16, for example, by a retaining tether (not shown) or other line attached thereto and to sheath cap 20 or valve cap 22. Cuff section 122 includes a loop 124 at a distal end thereof that passes through retaining hole 123 (see FIG. 5B) and is selectively engaged by the retaining tether. Retaining hole 123 is located at the substantially equal axial position as access hole 21 and offset therefrom by 90-degrees. As a result of the engagement between the loop and the retaining tether, cuff section 122 is prevented from being pushed along introducer 10 when the user inserts introducer 10 through, for example, a vessel wall with his hand in contact with sheet 18 or from friction provided by skin 1010, muscle 1020, or other encountered anatomy. Introducer 10 is inserted into the anatomy until cuff section 122 abuts the wall of vessel 1000, or other desired structure, as shown in FIG. 1. Such abutment provides increased resistance and tactile feedback indicating that cuff 122 is positioned at vessel 1000. Once positioned, the retaining tether may be removed to permit relative movement between sheet 18 (including cuff 122) and sheath 16.

Once sheet 18 is permitted to move relative to sheath 16, sheath 16 is further advanced into vessel 1000. During the moving of sheath 16, sheet 18 is held in place via the abutment of cuff section 122 against the wall of vessel 1000. Such relative movement results in flexible portion 19 being extracted from within sheath 16 through access hole 21 until flexible portion 19 is fully outside of sheath 16 and within vessel 1000.

Figure 2:
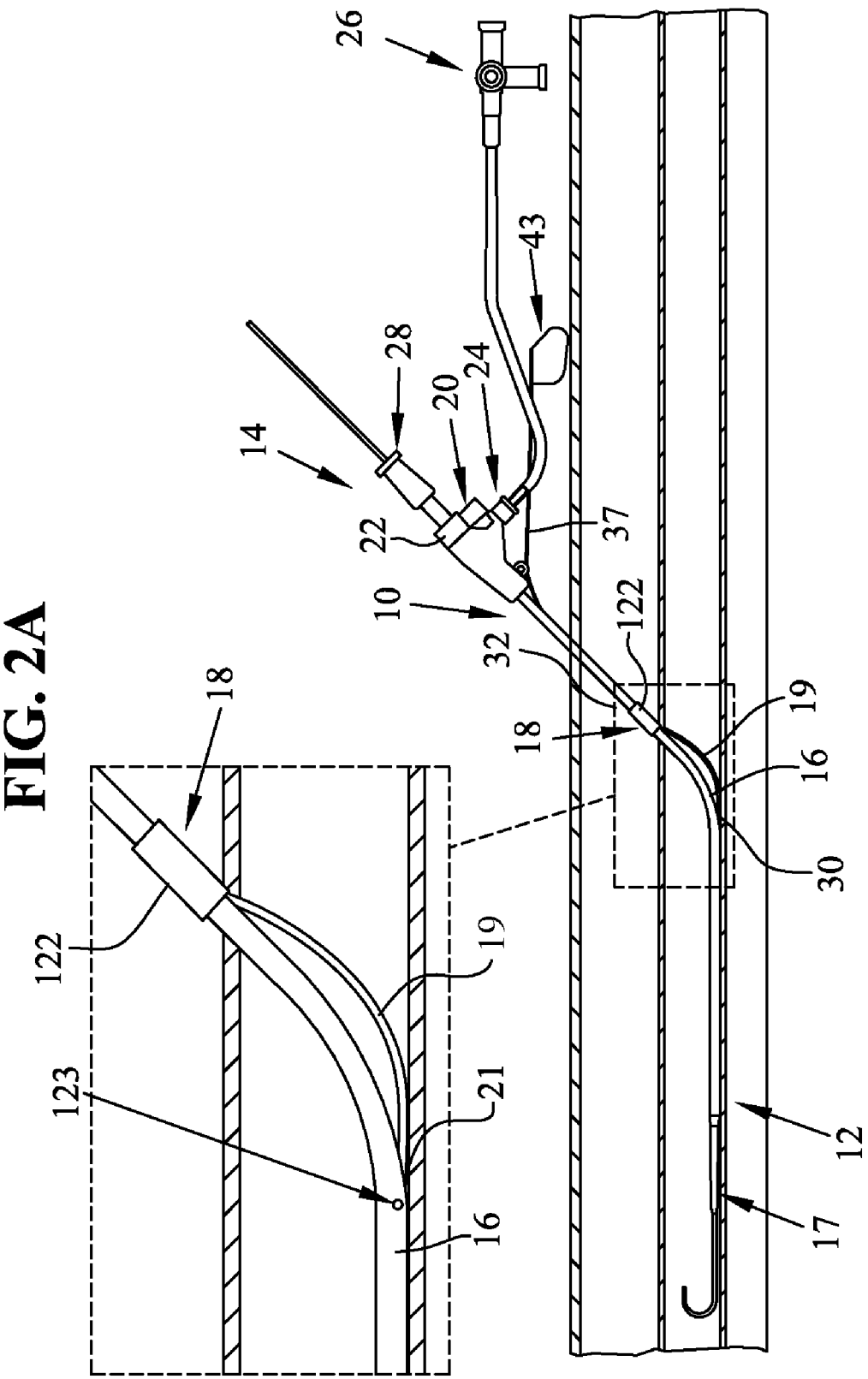

As shown in FIGS. 1 and 2, in one illustrative embodiment the sheet 18 has a second tether 37 attached at or near to the proximal end 32 of the sheet 18.

Tether 37 is attached to sheet 18, see FIGS. 4a, 4b, at or near proximal end 32 of sheet 18 and extends axially downwards through flexible portion 19 towards distal end 30 of sheet 18 and then back up through flexible portion 19 towards proximal end 32. Tether 37 is threaded through sheet 18 at many places. Thus, portions of tether 37 are inserted into blood vessel 1000 when the introducer 10 is pushed through the vessel wall and the proximal end 43 of tether 37 remains externally exposed.

Figure 3:
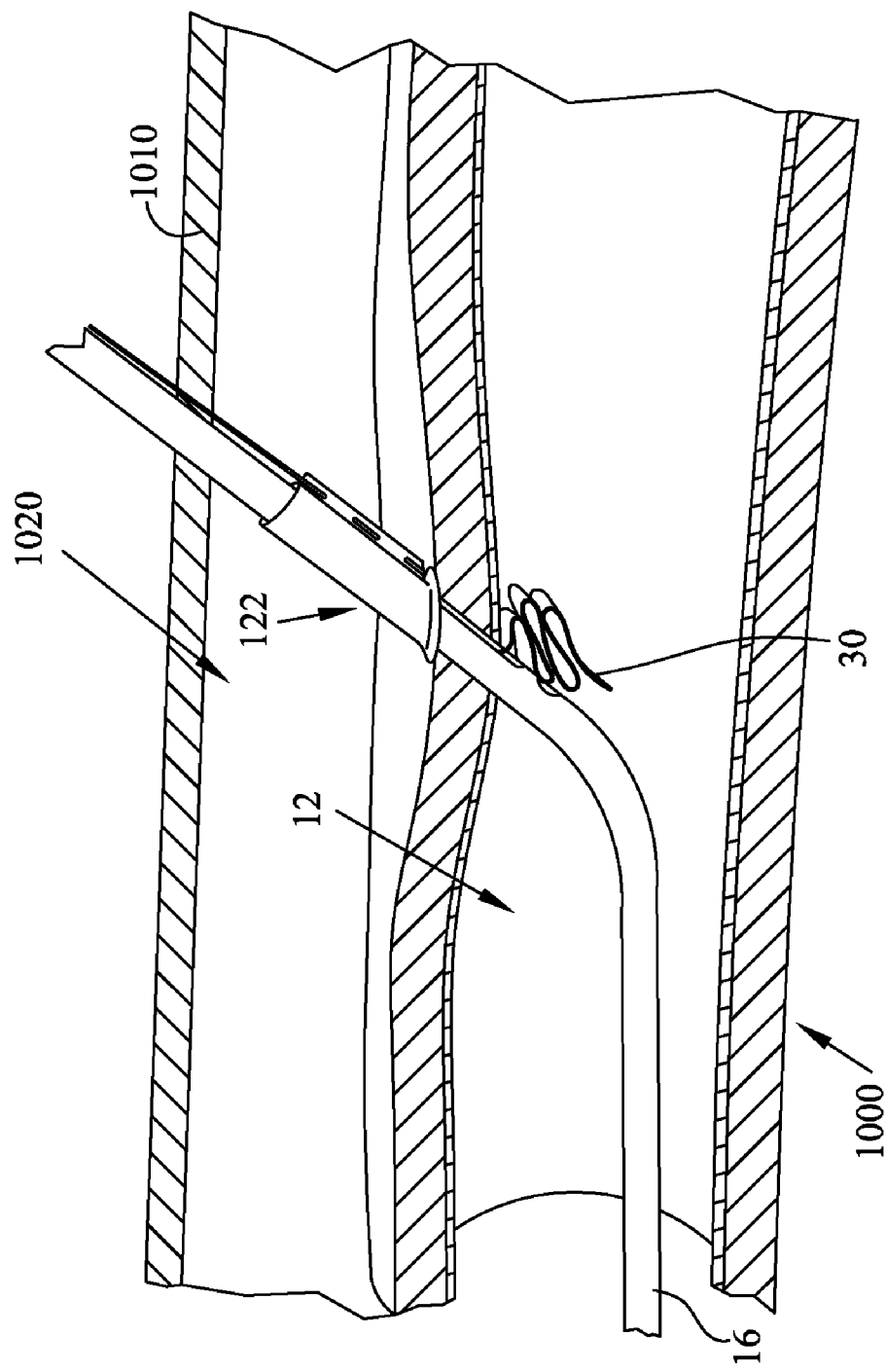
FIG. 3 illustrates the graft sheet secured in the tubular tissue structure.

Upon completion of the procedure, such as catheterization, or before completion if desired, proximal end 43 of tether 37 is pulled to gather distal end 30 of sheet 18 in the puncture site or on the inside of the vessel wall (see FIG. 3). Subsequent retracting of sheath 16 leaves gathered sheet 18 to form a plug at the puncture site of the vessel wall.

Sheet 18 may have any combination of tethers 37 and retaining tethers, or may lack one or more types of tethers. For example, the sheet 18 may lack a retaining tether. In this embodiment where only tether 37 is attached to the sheet 18, tether 37 is used to gather the sheet 18 in the puncture site and against the inside of the vessel wall.

Tethers with different functions (i.e., the retaining tether and tether 37) may have different indicia disposed thereon, such as different colors, so that the user can easily identify the tether with the desired function. Alternatively, tethers with different functions may have different caps attached to the externally exposed ends so that the tether with the desired function can be easily identified. In one illustrative embodiment, the tethers are made of resorbable thread and the tethers can be attached to the sheet 18 by any suitable means. For example, the tethers can be tied to the sheet 18, hooked to the sheet 18 by using hooks, barbs, etc. (e.g., for tethers with attachment points that remain externally exposed when the introducer 10 is inserted into the vessel wall), or woven/sewn into sheet 18 as shown in FIGS. 4a & 4b.

While certain embodiments of the present disclosure have been described in detail, those familiar with the art to which this disclosure relates will recognize various alternative designs and embodiments for practicing the disclosure as defined by the following claims.

What is claimed is:

1. A device for sealing a puncture site in a wall of a blood vessel comprising:
   an elongated element having a length adapted to be inserted into the puncture site and having a distal end, a proximal end, and an access port disposed in a wall of the elongated element spaced apart from and between the distal end and the proximal end, and
   a bioabsorbable member including an external portion disposed on the exterior of the elongated element, a portion extending through the access port of the elongated element, and an internal portion within the elongated element, the bioabsorbable member being releasably fixed to the elongated element.

2. The device of claim 1, wherein the elongated element has a tissue wall contact exterior portion.

3. The device of claim 1, wherein the length of the elongated element forms intravascular, intermediate and extracorporeal portions.

4. The device of claim 1, wherein the bioabsorbable member includes a cuff portion disposed on the exterior of the elongated element.

5. The device of claim 4, wherein the cuff portion forms a lumen that receives the elongated element therein.

6. The device of claim 4, wherein the cuff portion is slideable relative to the elongated element.

7. The device of claim 6, wherein sliding of the cuff relative to the elongated element causes at least some of the bioabsorbable member disposed within the elongated element to be withdrawn from the elongated element via the access port.

8. The device of claim 1, further including a removable tether that fixes the position of the external portion of the bioabsorbable member.

9. The device of claim 1, wherein the access port has a fixed location in the wall of the elongated element.

10. The device of claim 1, wherein the wall of the elongated element is made of a first material, the access port being defined in the wall such that all sides of the access port are defined by the first material.

11. The device of claim 1, wherein the elongated element further includes a lumen extending between distal end and the proximal end, at the internal portion having a first position in which the internal portion is disposed within the lumen.

12. The device of claim 1, wherein the access port is sized such that it extends less than all the way around the perimeter of the elongated element.

13. The device of claim 12, wherein the access port is sized such that it extends less than half way around the elongated element.

14. The device of claim 1, wherein the elongated element includes a portion of constant diameter, the access port being defined in the portion of constant diameter.

15. The device of claim 1, wherein the elongated element is of a homogenous construction.

16. The device of claim 1, wherein the access port defines a central port axis, the central port is not collinear with a central axis of the elongated element.

17. The device of claim 16, wherein the central port axis is not parallel with the central axis of the elongated element.

18. The device of claim 1, wherein the bioabsorbable member has a first position wherein the portion within the elongated element is longer than the portion disposed on the exterior of the elongated element.

19. The device of claim 1, wherein the elongated element is of fixed construction, having no moving parts.

20. The device of claim 1, wherein the elongated element has a fixed length.

21. The device of claim 1, wherein the elongated element is an introducer sheath.

22. The device of claim 1, further including a dilator partially disposed within the elongated element.

23. The device of claim 1, wherein the elongated element defines a central axis of the elongated element, the external portion of the bioabsorbable member being a first distance away from the central axis, the internal portion of the bioabsorbable member being a second distance away from the central axis, the first distance being different than the second distance.

24. The device of claim 1, wherein the internal portion of the bioabsorbable member is planar.

25. The device of claim 1, wherein the access port is disposed in the wall such that as the bioabsorbable member extends through the access port, the external portion is disposed on a exterior side of the wall and the interior portion is disposed on an interior side of the wall.

26. A method of sealing a puncture site in a wall of a blood vessel comprising:
   providing an elongated element having an outer wall and defining a lumen therein, the outer wall of the elongated element having a hole therein providing access to the lumen;
   releasably attaching a bioabsorbable member to the elongated element by inserting the bioabsorbable member into the hole in the wall of the elongated element such that a first portion of the bioabsorbable member is within the lumen of the elongated element and a second portion of the bioabsorbable member is outside of the lumen;
   placing the elongated element and attached bioabsorbable member into the anatomy of a patient;
   advancing the elongated element in the anatomy, wherein the advancement causes the first portion of the bioabsorbable member to evacuate the lumen of the elongated element.

27. The method of claim 26, wherein the second portion of the bioabsorbable member includes a cuff portion, and the cuff is positioned on the elongated element such that the step of placing the elongated element into the anatomy causes the cuff to abut the anatomy and the abutment of the cuff to anatomy prevents the cuff from advancing during the advancing step and causes the first portion of the bioabsorbable member to evacuate the lumen as the elongated element is advanced.

28. The method of claim 26, further including the step of retracting a tether coupled to the bioabsorbable member to cause the first portion of the bioabsorbable member to abut the puncture site.

29. The method of claim 26, wherein the placing step puts the entire bioabsorbable member within the anatomy.

30. The method of claim 26, wherein the placing step places the hole in the wall of the elongated element within the puncture site.

31. A device for sealing a puncture site comprising:
   an elongated element having a length adapted to be inserted into the puncture site and having a lumen therein, the elongated element further including a distal end access port, a proximal end access port, and a side access port, each of the access ports providing access to the lumen, and
   a bioabsorbable member including:
      an external portion disposed on the exterior of the elongated element,
      a portion extending through the side access port of the elongated element, and
      an internal portion disposed within the lumen, the bioabsorbable member being releasably fixed to the elongated element.

32. The device of claim 31, wherein the bioabsorbable member is pre-loaded onto the elongated element prior to use.

33. The device of claim 31, wherein the bioabsorbable member is a sheet of bioabsorbable material.

34. The device of claim 31, wherein the external portion of the bioabsorbable member forms a cuff having a lumen that receives the elongated element therein.

35. The device of claim 31, wherein the external portion, the portion extending through the side access port and the internal portion are of made of a substantially homogenous and continuous material.

36. The device of claim 31, further including a removable tether, wherein removing the tether permits the bioabsorbable member to move relative to the elongated element.

37. The device of claim 31, further including a tether that is woven into the bioabsorbable member prior to use.

\* \* \* \* \*